United States Patent
Santra et al.

(10) Patent No.: US 10,294,239 B2
(45) Date of Patent: May 21, 2019

(54) ERTUGLIFLOZIN CO-CRYSTALS AND PROCESS FOR THEIR PREPARATION

(71) Applicant: Sun Pharmaceutical Industries Limited, Mumbai, Maharashtra (IN)

(72) Inventors: Ramkinkar Santra, Paschim Medinipur (IN); Bala Krishna Reddy Bhogala, Kadapa (IN); Chandra Has Khanduri, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/576,452

(22) PCT Filed: May 24, 2016

(86) PCT No.: PCT/IB2016/053042
§ 371 (c)(1),
(2) Date: Nov. 22, 2017

(87) PCT Pub. No.: WO2016/189463
PCT Pub. Date: Dec. 1, 2016

(65) Prior Publication Data
US 2018/0155358 A1    Jun. 7, 2018

(30) Foreign Application Priority Data

May 25, 2015 (IN) .......................... 1471/DEL/2015
May 25, 2015 (IN) .......................... 1472/DEL/2015

(51) Int. Cl.
C07D 493/08 (2006.01)
A61P 3/10 (2006.01)
C07D 207/28 (2006.01)
C07D 207/22 (2006.01)
A61K 31/357 (2006.01)
(Continued)

(52) U.S. Cl.
CPC .......... *C07D 493/08* (2013.01); *A61K 31/357* (2013.01); *A61K 31/401* (2013.01); *A61P 3/10* (2018.01); *C07D 207/22* (2013.01); *C07D 207/28* (2013.01); *C07H 1/00* (2013.01); *C07H 9/04* (2013.01); *C07B 2200/13* (2013.01)

(58) Field of Classification Search
CPC .. C07D 493/08; C07D 207/22; C07D 207/28; A61P 3/10; A61K 31/357; A61K 31/401
USPC ........................................................ 514/420
See application file for complete search history.

(56) References Cited

U.S. PATENT DOCUMENTS 8,080,580 B2    12/2011    Mascitti et al.
8,609,622 B2    12/2013    Yang et al.
(Continued)

FOREIGN PATENT DOCUMENTS

WO    WO 2014159151 A1    10/2014

OTHER PUBLICATIONS

Mascitti; J. Med. Chem. 2011, 54, 2952-2960. (Year: 2011).*
(Continued)

*Primary Examiner* — Daniel R Carcanague
(74) *Attorney, Agent, or Firm* — William D. Hare

(57) ABSTRACT

The present invention relates to processes for the preparation of an ertugliflozin-L-pyroglutamic acid (1:1) and co-crystal ertugliflozin-L-proline (1:1) co-crystal. The present invention further relates to an ertugliflozin-L-proline (1:2) co-crystal, processes for its preparation, and its use for the treatment of type 2 diabetes mellitus.

11 Claims, 3 Drawing Sheets

(51) Int. Cl.
    *A61K 31/401*     (2006.01)
    *C07H 1/00*     (2006.01)
    *C07H 9/04*     (2006.01)

(56) References Cited

U.S. PATENT DOCUMENTS

| | | | |
|---|---|---|---|
| 9,676,741 B1* | 6/2017 | Santra | C07D 309/10 |
| 2010/0056618 A1* | 3/2010 | Mascitti | C07D 493/08 |
| | | | 514/456 |
| 2013/0137646 A1 | 5/2013 | Wienrich et al. | |
| 2014/0228303 A1 | 8/2014 | Jain et al. | |
| 2014/0303096 A1 | 10/2014 | Reiche et al. | |
| 2017/0158659 A1* | 6/2017 | Santra | C07D 309/10 |
| 2017/0342100 A1* | 11/2017 | Ali | C07F 7/1852 |

OTHER PUBLICATIONS

Bowles; Org. Process Res. Dev. 2014, 18, 66-81. (Year: 2014).*
Miao; Drug Metab Dispos 2013, 41, 445-456. (Year: 2013).*
International Search Report and Written Opinion dated Aug. 30, 2016 for PCT Patent Application No. PCT/IB2016/053042.
International Preliminary Report on Patentability dated Dec. 7, 2017 for PCT Patent Application No. PCT/IB2016/053042.
Vincent Mascitti et al, Journal of Medicinal Chemistry, "Discovery of a Clinical Candidate from the Structurally Unique Dioxa-bicyclo[3.2.1]octane Class of Sodium-Dependent Glucose Cotransporter 2 Inhibitors", 54(8): pp. 2952-2960 (2011).

* cited by examiner

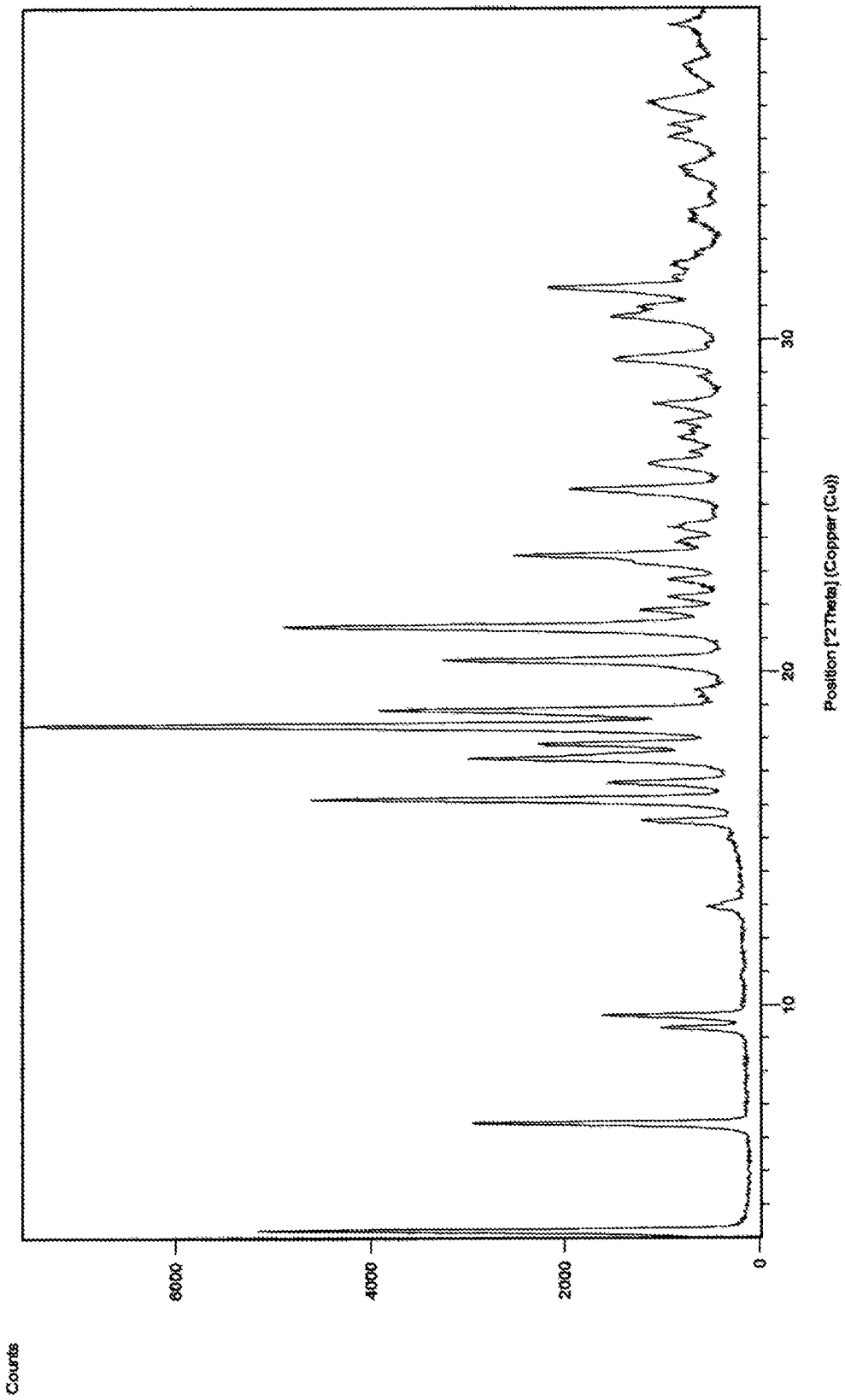
FIGURE 1: XRPD PATTERN OF ERTUGLIFLOZIN-L-PROLINE (1:2) CO-CRYSTAL

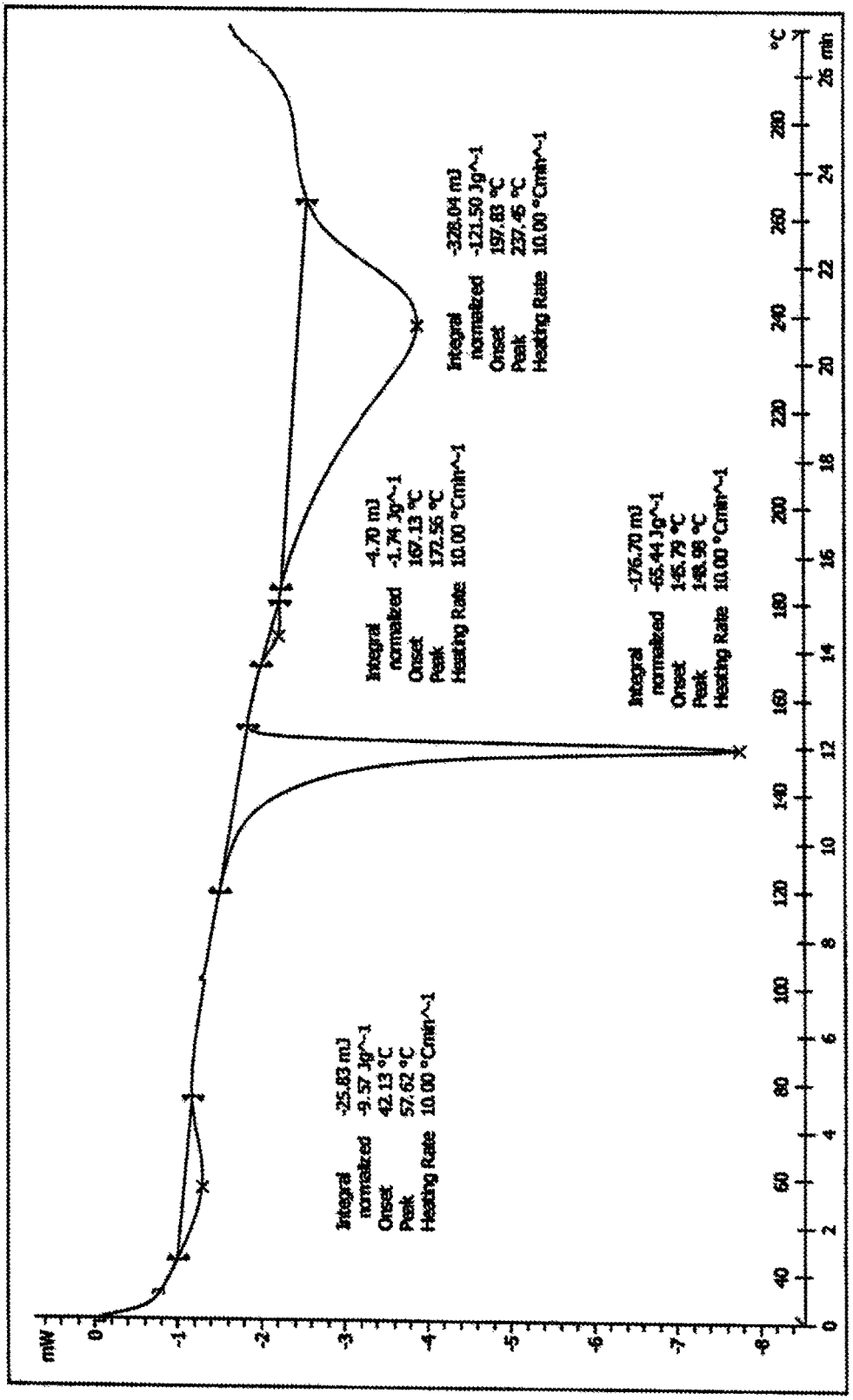
FIGURE 2: DSC OF ERTUGLIFLOZIN-L-PROLINE (1:2) CO-CRYSTAL

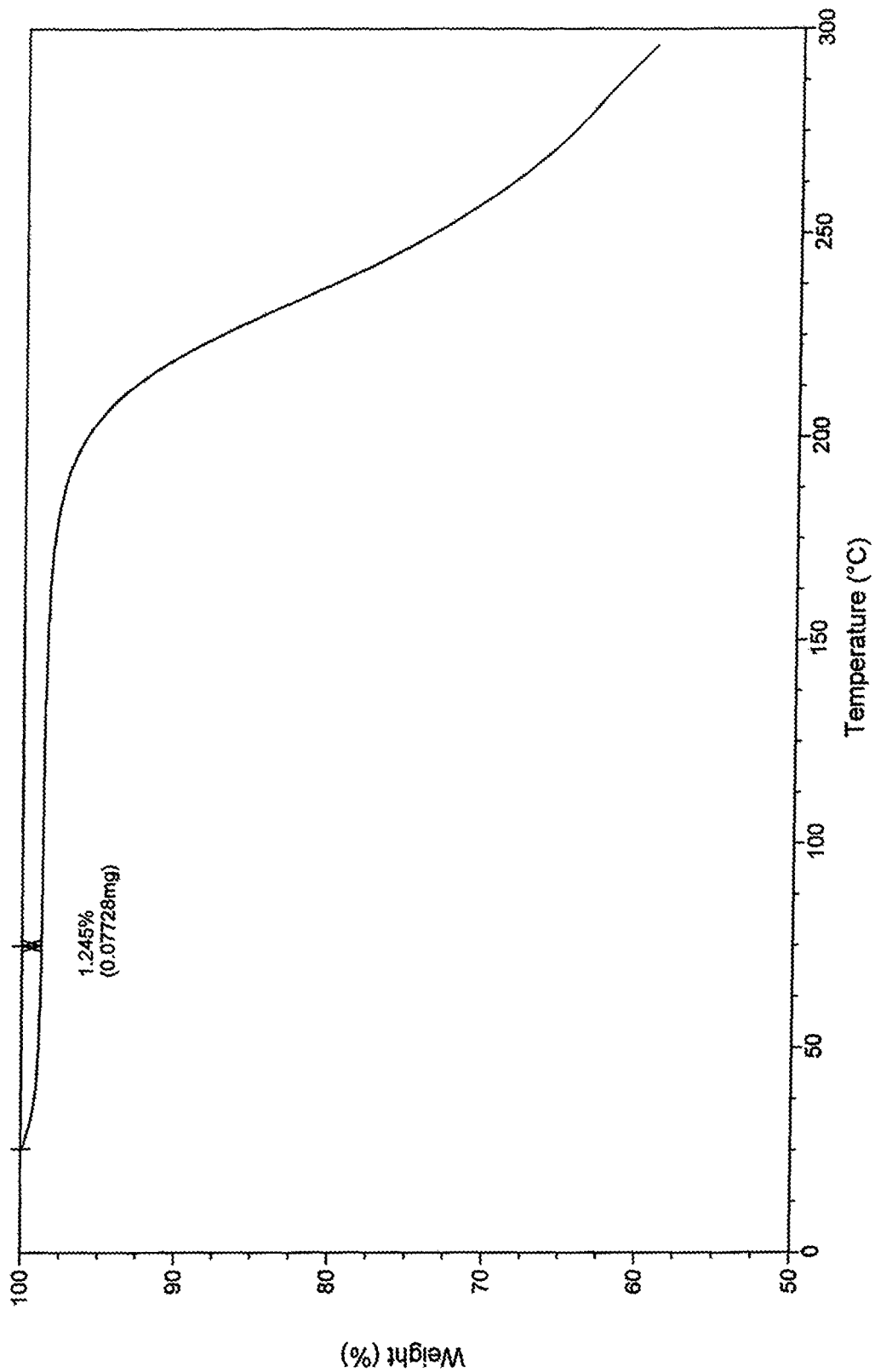
FIGURE 3: TGA OF ERTUGLIFLOZIN-L-PROLINE (1:2) CO-CRYSTAL

ERTUGLIFLOZIN CO-CRYSTALS AND PROCESS FOR THEIR PREPARATION

FIELD OF THE INVENTION

The present invention relates to processes for the preparation of an ertugliflozin-L-pyroglutamic acid (1:1) co-crystal and ertugliflozin-L-proline (1:1) co-crystal. The present invention further relates to an ertugliflozin-L-proline (1:2) co-crystal, processes for its preparation, and its use for the treatment of type 2 diabetes mellitus.

BACKGROUND OF THE INVENTION

Ertugliflozin chemically is (1S,2S,3S,4R,5S)-5-(4-chloro-3-(4-ethoxybenzyl)phenyl)-1-hydroxymethyl-6,8-dioxabicyclo[3.2.1]octane-2,3,4-triol, represented by Formula I.

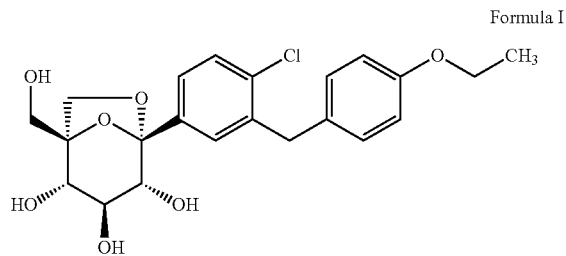 [SMILES: CCOc1ccc(Cc2cc([C@]34OC[C@](CO)(O3)[C@@H](O)[C@H](O)[C@H]4O)ccc2Cl)cc1]

Formula I

Ertugliflozin is a selective sodium glucose cotransporter 2 inhibitor for the treatment of type 2 diabetes mellitus.

U.S. Pat. No. 8,080,580 discloses processes for the preparation of ertugliflozin and its conversion to ertugliflozin-L-proline (1:1) co-crystal and ertugliflozin-L-pyroglutamic acid (1:1) co-crystal in solvents such as alcohol or aqueous alcohol. It also discloses the use of excess of L-proline and L-pyroglutamic acid.

PCT Publication No. WO 2014/159151 discloses a process for the preparation of ertugliflozin and its conversion to an ertugliflozin-L-pyroglutamic acid (1:1) co-crystal using excess L-pyroglutamic acid.

There is a need in the art for providing a process for the preparation of ertugliflozin co-crystals which is commercially viable and economical. Further, there is a need in the art for providing an ertugliflozin co-crystal with desirable physico-chemical properties such as solubility, rate of dissolution of the drug, chemical stability, melting point, and hygroscopicity.

SUMMARY OF THE INVENTION

The present invention relates to processes for the preparation of an ertugliflozin-L-pyroglutamic acid (1:1) co-crystal and ertugliflozin-L-proline (1:1) co-crystal. The present invention further relates to an ertugliflozin-L-proline (1:2) co-crystal, processes for its preparation, and its use for the treatment of type 2 diabetes mellitus.

BRIEF DESCRIPTION OF THE DRAWINGS

FIG. 1 depicts an X-Ray Powder Diffraction (XRPD) pattern of an ertugliflozin-L-proline (1:2) co-crystal.

FIG. 2 depicts a Differential Scanning Calorimetry (DSC) thermogram of an ertugliflozin-L-proline (1:2) co-crystal.

FIG. 3 depicts a Thermogravimetric Analysis (TGA) thermogram of an ertugliflozin-L-proline (1:2) co-crystal.

DETAILED DESCRIPTION OF THE INVENTION

Various embodiments and variants of the present invention are described hereinafter.

The term "about," as used herein, refers to any value which lies within the range defined by a number up to ±10% of the value.

The term "ambient temperature," as used herein, refers to any value which lies within the range between 20° C. and 30° C.

The term "contacting," as used herein, refers to bringing two or more components together by dissolving, mixing, suspending, blending, slurrying, or stirring.

The term "co-crystal," as used herein, refers to a stoichiometric multi component system comprising an active pharmaceutical ingredient (API) and a pharmaceutical co-crystal former, wherein the API and the pharmaceutical co-crystal former are connected by non-covalent interactions.

The term "co-crystal former," as used herein, refers to compounds which can form intermolecular interactions with an API and co-crystallize with it.

The term "solvent," as used herein, includes, for example, saturated or unsaturated hydrocarbons, alcohols, ethers, esters, halogenated hydrocarbons, carboxylic acids, ketones, amides, sulphoxides, water, or mixtures thereof.

The term "anhydrous solvent," as used herein, includes, for example, saturated or unsaturated hydrocarbons, alcohols, ethers, esters, halogenated hydrocarbons, carboxylic acids, ketones, amides, sulphoxides, or mixtures thereof.

Examples of saturated or unsaturated hydrocarbons include benzene, toluene, cyclohexane, and xylenes. Examples of alcohols include methanol, ethanol, 1-propanol, 1-butanol, 2-butanol, and tertiary alcohols having from one to six carbon atoms. Examples of ethers include diethyl ether, ethyl methyl ether, methyl tertiary butyl ether, diisopropyl ether, tetrahydrofuran, 2-methyltetrahydrofuran, and 1,4-dioxane. Examples of esters include ethyl acetate, methyl acetate, isopropyl acetate, and tertiary butyl acetate. Examples of halogenated hydrocarbons include dichloromethane and chloroform. Examples of carboxylic acids include formic acid, acetic acid, and propionic acid. Examples of ketones include acetone, 2-butanone, diethyl ketone, ethyl methyl ketone, and methyl iso-butyl ketone. Examples of amides include N,N-dimethylformamide and N,N-dimethylacetamide. Examples of sulphoxides include dimethyl sulphoxide and diethyl sulphoxide.

A first aspect of the present invention provides a process for the preparation of an ertugliflozin-L-pyroglutamic acid (1:1) co-crystal of Formula Ic,

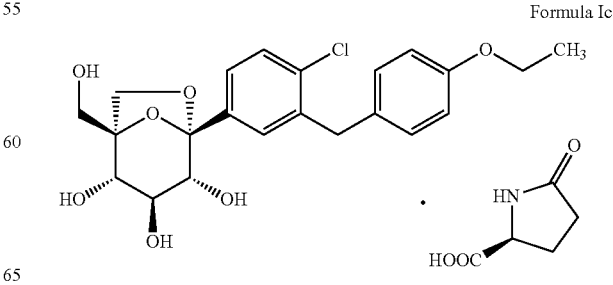

Formula Ic wherein the process comprises contacting ertugliflozin with L-pyroglutamic acid in the presence of a solvent, wherein the amount of L-pyroglutamic acid is about 1 mole equivalent to about 1.5 mole equivalents with respect to ertugliflozin.

Ertugliflozin used as the starting material can be prepared by methods known in the art, for example, as in U.S. Pat. No. 8,080,580.

The solvent is selected from the group comprising water, ethyl acetate, isopropyl acetate, 2-butanone, methyl isobutyl ketone, and methyl tertiary butyl ether.

In one embodiment of this aspect, the contacting of the ertugliflozin with the L-pyroglutamic acid is carried out at ambient temperature.

Preferably, the amount of L-pyroglutamic acid is about 1 mole equivalent to about 1.1 mole equivalents with respect to ertugliflozin.

The ertugliflozin-L-pyroglutamic acid (1:1) co-crystal may be isolated by employing one or more techniques selected from the group consisting of filtration, decantation, extraction, distillation, evaporation, chromatography, precipitation, concentration, crystallization, centrifugation, and recrystallization. The ertugliflozin-L-pyroglutamic acid (1:1) co-crystal may further be dried using conventional techniques, for example, drying, drying under vacuum, spray drying, freeze drying, air drying, or agitated thin film drying.

A second aspect of the present invention provides a process for the preparation of an ertugliflozin-L-proline (1:1) co-crystal of Formula Ib,

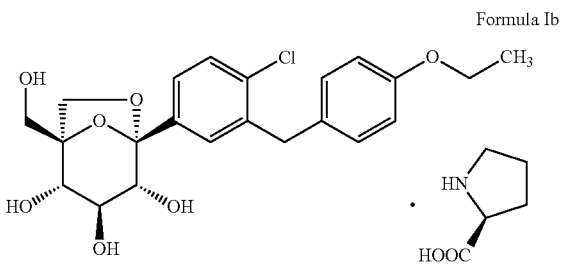 [SMILES: CCOc1ccc(Cc2cc([C@]34OC[C@](CO)(O3)[C@@H](O)[C@H](O)[C@H]4O)ccc2Cl)cc1 ; O=C(O)[C@@H]1CCCN1]

Formula Ib wherein the process comprises contacting ertugliflozin with L-proline in the presence of a solvent, wherein the amount of L-proline is about 1 mole equivalent to about 1.5 mole equivalents with respect to ertugliflozin.

Ertugliflozin used as the starting material can be prepared by methods known in the art, for example, as in U.S. Pat. No. 8,080,580.

Preferably, the solvent is ethyl acetate.

In one embodiment of this aspect, the contacting of the ertugliflozin with the L-proline is carried out at ambient temperature.

Preferably, the amount of L-proline is about 1 mole equivalent to about 1.1 mole equivalents with respect to ertugliflozin.

The ertugliflozin-L-proline (1:1) co-crystal may be isolated by employing one or more techniques selected from the group consisting of filtration, decantation, extraction, distillation, evaporation, chromatography, precipitation, concentration, crystallization, centrifugation, and recrystallization. The ertugliflozin-L-proline (1:1) co-crystal may further be dried using conventional techniques, for example, drying, drying under vacuum, spray drying, freeze drying, air drying, or agitated thin film drying.

A third aspect of the present invention provides an ertugliflozin-L-proline (1:2) co-crystal of Formula Ia.

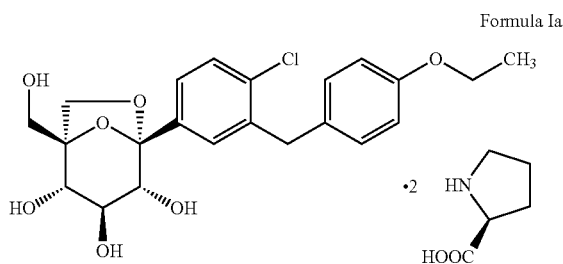 [SMILES: CCOc1ccc(Cc2cc([C@]34OC[C@](CO)(O3)[C@@H](O)[C@H](O)[C@H]4O)ccc2Cl)cc1 ; O=C(O)[C@@H]1CCCN1]

Formula Ia

In one embodiment of this aspect, the ertugliflozin-L-proline (1:2) co-crystal is characterized by an X-ray powder diffraction (XRPD) pattern substantially as depicted in FIG. 1.

In another embodiment of this aspect, the ertugliflozin-L-proline (1:2) co-crystal is characterized by an XRPD having interplanar spacing (d) values at about 27.3, 5.5, 4.8, 4.7, and 4.2 Å. The ertugliflozin-L-proline (1:2) co-crystal is further characterized by an XRPD having additional interplanar spacing (d) values at about 13.7, 5.1, 4.4, 3.8, 3.5, and 2.8 Å.

In yet another embodiment of this aspect, the ertugliflozin-L-proline (1:2) co-crystal is characterized by an XRPD having characteristic peak values at about 3.2, 16.2, 18.4, 18.9, and 21.4±0.2° 2θ. The ertugliflozin-L-proline (1:2) co-crystal is further characterized by an XRPD having additional characteristic peak values at about 6.5, 17.4, 20.4, 23.5, 25.5, and 31.6±0.2° 2θ.

Table 1 provides the 2θ values, the corresponding d-spacing values (Å), and the relative intensity of the ertugliflozin-L-proline (1:2) co-crystal.

TABLE 1

| Position (°2θ) | d-spacing (Å) | Relative intensity (%) |
| --- | --- | --- |
| 3.2 | 27.3 | 68.9 |
| 6.5 | 13.7 | 38.3 |
| 9.3 | 9.5 | 11.1 |
| 9.7 | 9.1 | 19.6 |
| 12.9 | 6.8 | 5.2 |
| 15.5 | 5.7 | 14.2 |
| 16.2 | 5.5 | 57.6 |
| 16.7 | 5.3 | 18.8 |
| 17.4 | 5.1 | 38.3 |
| 17.9 | 5.0 | 28.6 |
| 18.4 | 4.8 | 100.0 |
| 18.9 | 4.7 | 50.5 |
| 19.5 | 4.6 | 6.7 |
| 20.4 | 4.4 | 41.2 |
| 21.4 | 4.2 | 63.9 |
| 21.9 | 4.1 | 14.4 |
| 22.3 | 4.0 | 10.1 |
| 22.8 | 3.9 | 10.6 |
| 23.5 | 3.8 | 29.6 |
| 23.9 | 3.7 | 8.6 |
| 24.4 | 3.6 | 8.6 |
| 25.5 | 3.5 | 23.3 |
| 26.3 | 3.4 | 12.7 |
| 26.6 | 3.4 | 7.5 |
| 27.0 | 3.3 | 8.8 |
| 27.5 | 3.2 | 9.2 |
| 28.1 | 3.2 | 12.1 |
| 28.8 | 3.1 | 5.4 |
| 29.4 | 3.0 | 17.7 |
| 30.7 | 2.9 | 18.3 |
| 31.0 | 2.9 | 14.1 |
| 31.6 | 2.8 | 26.6 |
| 32.3 | 2.8 | 9.4 |
| 33.6 | 2.7 | 7.01 |
| 33.9 | 2.6 | 7.2 |

TABLE 1-continued

| Position (°2θ) | d-spacing (Å) | Relative intensity (%) |
|---|---|---|
| 35.2 | 2.6 | 8.5 |
| 36.1 | 2.5 | 9.9 |
| 36.4 | 2.5 | 10.0 |
| 37.2 | 2.4 | 12.5 |
| 38.3 | 2.4 | 8.0 |
| 39.5 | 2.3 | 9.7 |

In another embodiment of this aspect, the ertugliflozin-L-proline (1:2) co-crystal is characterized by a differential scanning calorimetric (DSC) thermogram having endothermic peaks at about 148° C. and 236° C., as depicted in FIG. 2.

In another embodiment of this aspect, the ertugliflozin-L-proline (1:2) co-crystal is characterized by a thermogravimetric analysis (TGA) thermogram as depicted in FIG. 3.

A fourth aspect of the present invention provides a process for the preparation of an ertugliflozin-L-proline (1:2) co-crystal of Formula Ia, Formula Ia wherein the process comprises contacting ertugliflozin with L-proline in the presence of an anhydrous solvent.

Ertugliflozin used as the starting material can be prepared by methods known in the art, for example, as in U.S. Pat. No. 8,080,580.

Preferably, the anhydrous solvent is selected from the group comprising 2-butanone, ethyl acetate, and a mixture of ethanol and methyl tertiary butyl ether.

In one embodiment of this aspect, the contacting of ertugliflozin with L-proline is carried out at ambient temperature.

In another embodiment of this aspect, the amount of L-proline is about 0.5 mole equivalent to about 5 mole equivalents with respect to ertugliflozin. Preferably, the amount of L-proline is about 0.8 mole equivalent to about 2 mole equivalents with respect to ertugliflozin.

In yet another embodiment of this aspect, the water content of the anhydrous solvent is not more than 0.15%. Preferably, the water content of the anhydrous solvent is not more than 0.1%.

The ertugliflozin-L-proline (1:2) co-crystal may be isolated by employing one or more techniques selected from the group consisting of filtration, decantation, extraction, distillation, evaporation, chromatography, precipitation, concentration, crystallization, centrifugation, and recrystallization. The ertugliflozin-L-proline (1:2) co-crystal may further be dried using conventional techniques, for example, drying, drying under vacuum, spray drying, freeze drying, air drying, or agitated thin film drying.

A fifth aspect of the present invention provides a pharmaceutical composition comprising an ertugliflozin-L-proline (1:2) co-crystal and one or more pharmaceutically acceptable carriers, diluents, or excipients.

A sixth aspect of the present invention provides the use of an ertugliflozin-L-proline (1:2) co-crystal for the treatment of type 2 diabetes mellitus.

While the present invention has been described in terms of its specific aspects, certain modifications and equivalents will be apparent to those skilled in the art and are intended to be included within the scope of the present invention.

Methods:

The XRPD of the samples were determined by using Instrument: PANalytical®; Model: X'pert PRO; Detector: X'celerator®; Step size: 0.02; Range: 3-40 degree 2 theta; CuKα radiation at 45 kV and 40 mA.

The DSC of the samples were determined using a Mettler-Toledo® 821e. Data collection parameters: Scanning rate: 10° C./min; Temperature: 30° C. to 300° C.

The TGA of the samples were determined by using a TA® Q500 between 30° C. and 300° C. at 10° C./min scan rate.

The following examples are for illustrative purposes only and should not be construed as limiting the scope of the invention in any way.

EXAMPLES

Example 1

Preparation of Ertugliflozin-L-proline (1:1) Co-crystal

Ertugliflozin (0.5 g) and L-proline (0.131 g) were added to ethyl acetate (3 mL, water content ~0.18%), and then the mixture was stirred for 1 hour at 25° C. to 30° C. Ethyl acetate (2 mL) was added to the reaction mixture, and the mixture was stirred for 16 hours. The obtained solid was filtered, and then dried under vacuum at 25° C. to 30° C.

Yield: 0.61 g

Example 2

Preparation of Ertugliflozin-L-pyroglutamic acid (1:1) Co-crystal

Ertugliflozin (0.5 g) was added to a solution of L-pyroglutamic acid (2.2 mL; L-pyroglutamic acid (0.563 g) dissolved in water (2.73 mL)), and then the solution was stirred for 1.5 hours at 25° C. to 30° C. Water (1.5 mL) was added to the reaction mixture, and then the mixture was stirred for 1 hour. The obtained solid was filtered, and then dried under vacuum at 40° C. for 6 hours.

Yield: 0.472 g

Example 3

Preparation of Ertugliflozin-L-pyroglutamic acid (1:1) Co-crystal

Ertugliflozin (0.225 g) and L-pyroglutamic acid (0.067 g) were added to ethyl acetate (3 mL), and then the mixture was stirred for 3 hours at 25° C. to 30° C. Ethyl acetate (2 mL) was added to the reaction mixture, and the mixture was stirred for 4 hours. The obtained solid was filtered, and then washed with ethyl acetate (3 mL). The solid was dried under vacuum at 25° C. to 30° C. for 1 hour, and then at 40° C. for 5 hours.

Yield: 0.2 g

Example 4

Preparation of Ertugliflozin-L-pyroglutamic acid (1:1) Co-crystal

Ertugliflozin (0.225 g) and L-pyroglutamic acid (0.067 g) were added to isopropyl acetate (3 mL), and then the mixture was stirred for 3 hours at 25° C. to 30° C. Isopropyl acetate (2 mL) was added to the reaction mixture, and the mixture was stirred for 4 hours. The obtained solid was filtered, and then washed with isopropyl acetate (4 mL). The solid was dried under vacuum at 25° C. to 30° C. for 1 hour, and then at 40° C. for 5 hours.

Yield: 0.22 g

Example 5

Preparation of Ertugliflozin-L-pyroglutamic acid (1:1) Co-crystal

Ertugliflozin (0.225 g) and L-pyroglutamic acid (0.067 g) were added to 2-butanone (3 mL), and then the mixture was stirred for 3 hours at 25° C. to 30° C. 2-Butanone (2 mL) was added to the reaction mixture, and the mixture was stirred for 4 hours. The obtained solid was filtered, and then washed with 2-butanone (3 mL). The solid was dried under vacuum at 25° C. to 30° C. for 1 hour, and then at 40° C. for 5 hours.

Yield: 0.14 g

Example 6

Preparation of Ertugliflozin-L-pyroglutamic acid (1:1) Co-crystal

Ertugliflozin (0.225 g) and L-pyroglutamic acid (0.067 g) were added to methyl isobutyl ketone (3 mL), and then the mixture was stirred for 3 hours at 25° C. to 30° C. Methyl isobutyl ketone (2 mL) was added to the reaction mixture, and the mixture was stirred for 4 hours. The obtained solid was filtered, and then washed with methyl isobutyl ketone (4 mL). The solid was dried under vacuum at 25° C. to 30° C. for 1 hour, and then at 40° C. for 5 hours.

Yield: 0.23 g

Example 7

Preparation of Ertugliflozin-L-proline (1:2) Co-crystal

Ertugliflozin (0.756 g) and L-proline monohydrate (0.4 g) were added to ethanol (4 mL), and then the mixture was heated in a water bath to 70° C. The solution was cooled to 25° C. to 30° C. Methyl tertiary butyl ether (30 mL) was added in three lots (10 mL each), and the mixture was stirred for 6 hours at 25° C. to 30° C. to obtain a solid. The solid so obtained was filtered under nitrogen atmosphere. The solid was washed with methyl tertiary butyl ether (20 mL), and then dried under vacuum at 25° C. to 30° C. for 4 hours, and then at 40° C. for 6 hours.

Yield: 0.862 g $^1$H NMR (400 MHz, MeOD): δ ppm 1.35-1.39 (t, 3H), 1.96-2.02 (m, 4H), 2.12-2.15 (m, 2H), 2.28-2.30 (m, 2H), 3.22-3.23 (m, 2H), 3.25-3.33 (m, 2H), 3.54-3.61 (m, 4H), 3.64-3.67 (m, 2H), 3.68-3.86 (m, 4H), 3.95-4.03 (m, 2H), 4.04-4.16 (d, 1H), 6.80-6.82 (d, 2H), 7.09-7.11 (d, 2H), 7.37-7.46 (m, 2H), 7.47 (s, 1H).

Example 8

Preparation of Ertugliflozin-L-proline (1:2) Co-crystal

Ertugliflozin (0.75 g) and L-proline (0.393 g) were added to 2-butanone (9 mL) at 25° C. to 30° C., and then the mixture was stirred for 30 minutes to occur precipitation. The mixture was stirred for 5 hours at 25° C. to 30° C. to obtain a solid. The solid so obtained was filtered under nitrogen atmosphere. The solid was washed with 2-butanone (5 mL), and then dried under vacuum at 25° C. to 30° C. for 4 hours, and then at 40° C. for 6 hours.

Yield: 0.918 g

Example 9

Preparation of Ertugliflozin-L-proline (1:2) Co-crystal

Ertugliflozin (0.25 g) and L-proline monohydrate (0.152 g) were added to ethyl acetate (3.5 mL, water content <0.06%), and then the mixture was stirred for 6 hours at 25° C. to 30° C. The mixture was filtered, and then dried under vacuum at 25° C. to 30° C.

Yield: 0.295 g

Example 10

Preparation of Ertugliflozin-L-proline (1:2) Co-crystal

Ertugliflozin (0.25 g) and L-proline monohydrate (0.067 g) were added to ethanol (1 mL), and then the mixture was heated in a water bath to 70° C. The solution was cooled to 25° C. to 30° C. Methyl tertiary butyl ether (10 mL) was added, and the mixture was stirred for 5 hours at 25° C. to 30° C. to obtain a solid. The solid so obtained was filtered under nitrogen atmosphere. The solid was dried under vacuum at 25° C. to 30° C. for 6 hours, and then at 40° C. for 4 hours.

Yield: 0.19 g

Example 11

Preparation of Ertugliflozin-L-proline (1:2) Co-crystal

Ertugliflozin (0.25 g) and L-proline monohydrate (0.201 g) were added to ethanol (1.5 mL), and then the mixture was heated in a water bath to 70° C. The solution was cooled to 25° C. to 30° C. Methyl tertiary butyl ether (10 mL) was added, and the mixture was stirred for 5 hours at 25° C. to 30° C. to obtain a solid. The solid so obtained was filtered under nitrogen atmosphere. The solid was dried under vacuum at 25° C. to 30° C. for 6 hours, and then at 40° C. for 4 hours.

Yield: 0.33 g

We claim:

1. Ertugliflozin-L-proline (1:2) co-crystal of Formula Ia

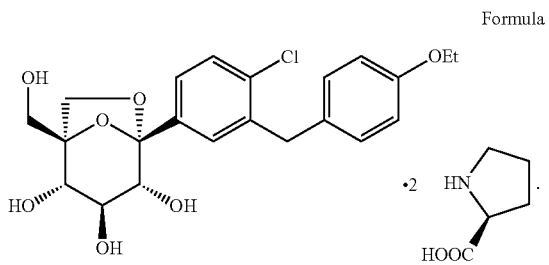

Formula Ia

2. The ertugliflozin-L-proline (1:2) co-crystal according to claim 1, characterized by an X-ray powder diffraction (XRPD) pattern as depicted in FIG. 1.

3. The ertugliflozin-L-proline (1:2) co-crystal according to claim 1, characterized by an XRPD having interplanar spacing (d) values at about 27.3, 5.8, 4.8, 4.7, and 4.2 Å.

4. The ertugliflozin-L-proline (1:2) co-crystal according to claim 3, characterized by an XRPD having additional interplanar spacing (d) values at about 13.7, 5.1, 4.4, 3.8, 3.5, and 2.8 Å.

5. The ertugliflozin-L-proline (1:2) co-crystal according to claim 1, characterized by an XRPD having characteristic peak values at about 3.2, 16.2, 18.4, 18.9, and 21.4±0.2° 2θ.

6. The ertugliflozin-L-proline (1:2) co-crystal according to claim 5, further characterized by an XRPD having additional characteristic peak values at about 6.5, 17.4, 20.4, 23.5, 25.5, and 31.6±0.2° 2θ.

7. The ertugliflozin-L-proline (1:2) co-crystal according to claim 1, characterized by a differential scanning calorimetric (DSC) thermogram having endothermic peaks at about 148° C. and 236° C. as depicted in FIG. 2.

8. The ertugliflozin-L-proline (1:2) co-crystal according to claim 1, characterized by a thermogravimetric analysis (TGA) thermogram as depicted in FIG. 3.

9. A process for the preparation of an ertugliflozin-L-proline (1:2) co-crystal of Formula Ia of claim 1,

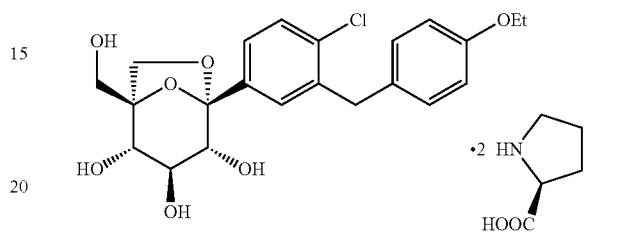

Formula Ia wherein the process comprises contacting ertugliflozin with L-proline in the presence of an anhydrous solvent.

10. A pharmaceutical composition comprising an ertugliflozin-L-proline (1:2) co-crystal of claim 1 and one or more pharmaceutically acceptable carriers, diluents, or excipients.

11. A method of treating type 2 diabetes mellitus, the method comprising administering a therapeutically effective amount of ertugliflozin-L-proline (1:2) co-crystal of claim 1.

* * * * *